(12) United States Patent
Sorrels

(10) Patent No.: US 6,807,681 B2
(45) Date of Patent: Oct. 26, 2004

(54) PROTECTIVE GUARDS FOR FINGER AND THUMBS

(76) Inventor: m. Kevin Sorrels, 7919 Braes Meadow, Houston, TX (US) 77071

( * ) Notice: Subject to any disclaimer, the term of this patent is extended or adjusted under 35 U.S.C. 154(b) by 0 days.

(21) Appl. No.: 09/990,777

(22) Filed: Nov. 21, 2001

(65) Prior Publication Data

US 2002/0134392 A1 Sep. 26, 2002

Related U.S. Application Data

(60) Provisional application No. 60/252,523, filed on Nov. 21, 2000.

(51) Int. Cl.$^7$ ............................................... A41D 13/00
(52) U.S. Cl. ............................................................ 2/21
(58) Field of Search ................................ 2/16, 21, 163, 2/161.7; 128/878, 880; 602/5, 21, 22; 132/73

(56) References Cited

U.S. PATENT DOCUMENTS

| | | |
|---|---|---|
| 136,640 A | 3/1873 | Bond |
| 1,316,292 A | 9/1919 | Fleming |
| 1,337,957 A | 4/1920 | Rasmussen |
| 1,388,618 A | 8/1921 | Stein et al. |
| 2,379,624 A | 7/1945 | Chisnell |
| 2,538,889 A | 1/1951 | Swarin |
| 2,935,354 A | 5/1960 | Chapman |
| 3,070,804 A | 1/1963 | Parrilla |
| 3,228,033 A | 1/1966 | Ames et al. |
| 3,728,736 A | 4/1973 | Pugh |
| 4,127,222 A | 11/1978 | Adams |
| 4,433,439 A | 2/1984 | Sidman et al. |
| 4,689,828 A | 9/1987 | Brewer |
| 4,694,843 A | 9/1987 | Casenhiser |
| 4,796,302 A | 1/1989 | Davis et al. |
| 4,858,245 A | 8/1989 | Sullivan et al. |
| 4,901,372 A | 2/1990 | Pierce |
| 4,958,384 A * | 9/1990 | McCrane ..................... 2/161.6 |
| 4,985,038 A | 1/1991 | Lyell |
| 5,070,543 A | 12/1991 | Beck |
| 5,133,087 A * | 7/1992 | Machida et al. ............... 2/168 |
| 5,231,700 A * | 8/1993 | Cutshall ..................... 2/161.7 |
| 5,450,626 A | 9/1995 | Sorrels |
| D373,656 S | 9/1996 | Sorrels |
| 5,685,014 A * | 11/1997 | Dapsalmon ...................... 2/16 |
| 5,842,227 A | 12/1998 | Rabin et al. |
| 5,924,428 A | 7/1999 | Song |
| RE36,778 E | 7/2000 | DeLeo |
| 6,237,148 B1 | 5/2001 | Graham |

* cited by examiner

Primary Examiner—Tejash Patel
(74) Attorney, Agent, or Firm—Meyertons, Hood, Kivlin, Kowert & Goetzel, P.C.; Eric B. Meyertons

(57) ABSTRACT

A protective guard for a finger or thumb may be used during a medical procedure. The protective guard may inhibit needle or instrument puncture of a medical practitioner's skin during a medical procedure. The protective guard may include a puncture resistant portion and a less puncture resistant portion. The material used to form the puncture resistant portion and the less puncture resistant portion may be chosen so that the guard provides a large degree of penetration resistance while still remaining flexible. The color of the puncture resistant portion may be different than the color of the less puncture resistant portion to provide a user with a visual indication of the puncture resistant portions of the protective guard.

34 Claims, 3 Drawing Sheets

PROTECTIVE GUARDS FOR FINGER AND THUMBS

PRIORITY CLAIM

This application claims priority to U.S. Provisional Patent Application No. 60/252,523 entitled "Protective Guards for Fingers and Thumbs" filed on Nov. 21, 2000.

BACKGROUND OF THE INVENTION

1. Field of the Invention

This invention relates generally to protective guards, and embodiments relate to protective guards for fingers and thumbs that inhibit skin penetration by needles and/or instruments.

2. Description of Related Art

Medical practitioners, including but not limited to doctors, physician assistants, nurses, dentists, and dental assistants may use instruments, implants and/or needles during medical procedures. Medical procedures may include, but are not limited to, surgical procedures and operations; dental procedures and operations; and injection or drawing of fluids using needles. A risk exists that a medical practitioner's skin may be punctured or penetrated during a medical procedure, resulting in a percutaneous injury. A medical practitioner's skin may also be punctured or penetrated during disposal or cleaning of needles or medical instruments previously used in a medical procedure. The medical practitioner and/or patient may be subject to infection or disease including, but not limited to, staphylococcus, hepatitis, and acquired immunodeficiency syndrome (AIDS) due to an inadvertent puncture of the medical practitioner. With or without transmission of a disease or pathogen, a skin puncture or other wound may be traumatic to the medical practitioner. There is a need to protect medical practitioners and patients from the risk of infection and pathogens due to skin punctures or wounds of the medical practitioner during a medical procedure.

Surgical gloves may be used by medical practitioners to lessen the risk of transferring blood-borne and other pathogens during medical procedures. Some medical practitioners use two gloves on each hand to reduce the risk of glove failure and skin punctures during medical procedures. Surgical gloves typically do not provide adequate protection from penetration of skin by sharps. Sharps may include, but are not limited to, hypodermic needles; medical, dental and laboratory instruments; and burs and sharp edges or projections of hard tissue and prostheses. Studies show that puncture wounds of medical practitioners often occur on backs of a medical practitioner's fingers or thumb. Puncture wounds may occur predominantly to the index finger, thumb and middle finger. For example, a medical practitioner may hold a syringe in a dominant hand while retracting, isolating, or palpating tissue with the other hand. A sudden movement by the patient may cause the medical practitioner to accidentally puncture the back of a finger or thumb of the non-dominant hand.

Finger coverings and/or hand protectors may be used to reduce the risk of inadvertent skin punctures in non-medical applications. U.S. Pat. No. 3,228,033 issued to Ames, et al., discloses a finger guard for use while pinning garments. U.S. Pat. No. 4,689,828 issued to Brewer, discloses a finger protector for hair stylists' fingers that includes a wristband joined to a two-finger protector. The two-finger protector has open ends for the fingers to extend through. U.S. Pat. No. 4,858,245 issued to Sullivan, et al., discloses an armored glove finger including a rib knit tubular member having an open end and a closed end.

Finger coverings and/or hand protectors may be used in medical applications. U.S. Pat. No. 4,901,372 issued to Pierce, which is incorporated by reference as if fully set forth herein, discloses a trilaminar glove with inner and outer barrier layers and a central foam layer. The trilaminar construction may reduce the risk of a puncture through the glove. U.S. Pat. No. 4,985,038 issued to Lyell, which is incorporated by reference as if fully set forth herein, discloses a needle stop surgical instrument comprising a finger housing, a needle receiving space, and a handle. The finger housing receives a finger, and the needle receiving space receives and guides a needle. The handle may be grasped between the remaining fingers of the hand and the palm of the hand to allow maneuvering. U.S. Pat. No. 5,070,543 issued to Beck, which is incorporated by reference as if fully set forth herein, discloses surgical gloves having protective pads placed at selected areas of the surgical gloves. The selected areas of the surgical gloves may include the fingertips and the palms.

U.S. Pat. No. 5,450,626 issued to Sorrels, which is incorporated by reference as if fully set forth herein, discloses protective finger coverings that have flexible and puncture resistant construction. A finger covering may include a puncture resistant, protective surface on a dorsal or back side of the covering. As used herein, dorsal in relation to a finger means that portion of the finger opposite the palm of the hand, and ventral means that portion of the finger adjacent the palm of the hand when a fist is formed. The finger guide may also include a retentive or elastic layer that may function to hold the covering on a user's finger or thumb. The retentive layer may be located on a ventral side of the covering. The covering may be open-ended to allow a portion of a user's thumb or finger to extend through the covering. The portion of the user's thumb or finger that extends through the covering may allow the user to retain tactile sense while using the covering. The covering may be rotated during use to change the position of the protective surface.

Finger coverings and hand protectors may have several disadvantages. Finger coverings and/or hand protectors may limit finger and/or hand flexibility of the user. Finger coverings and/or hand protectors may limit a user's sense of touch during a procedure. A user's sense of touch may be import during a medical procedure, especially if palpation of various surfaces of a treatment area is required during the procedure. A medical practitioner may need to retain a tactile sense during a medical procedure to control a patient and to maintain awareness of locations of sharp portions of instruments, inserts, and/or needles. Additionally, the use of finger and/or hand protectors may be limited by the amount of working space available within the patient. For example, a dentist does not have a large amount of working space within a patient's mouth. Also, a doctor typically does not have a large amount of working space within a patient during an invasive medical procedure.

SUMMARY OF THE INVENTION

A protective guard for a digit of a hand may include a flexible and penetration resistant construction. A digit may be a finger or a thumb. The protective guard may inhibit punctures or other wounds of a medical practitioner during a medical procedure. The protective guard may be formed as an elongated tubular member that covers the middle and terminal phalanges of a finger or thumb. When the protective guard is positioned on a finger, the protective guard may extend from just beyond the fingertip to just past the medial finger joint. An end of the protective guard nearest the medial joint may be contoured to allow bending of the medial joint. An end of the protective guard nearest the fingertip may be shaped to avoid covering a large portion of the pad of the fingertip. Leaving a large portion of the pad of the fingertip uncovered may promote retention of a user's tactile sense.

A protective guard may include a ventral (or front) portion and a dorsal (or back) portion. The ventral portion may include elastic material that functions to retain the protective guard on a medical practitioner's finger or thumb. The dorsal portion may include penetration and puncture resistant material. A protective guard may have a ring-shaped cross sectional form. An inner diameter of the protective guard may be smaller than a diameter of a finger or thumb upon which the protective guard is placed. The protective guard may form a seal with a user's hand that inhibits fluid from contacting the portion of a user's hand or finger that is covered by the protective guard. The elastic properties of the material may hold the protective guard on a finger or thumb when the guard is positioned on the finger or thumb. The elastic properties of the protective guard and/or the shape of the protective guard may allow the protected finger or thumb to be bent or flexed. Alternatively, grooves may be formed in a portion of the protective guard to allow the guard to flex when the finger or thumb is bent or flexed.

A dorsal portion of a protective guard may be protective material that is puncture and penetration resistant. The dorsal portion may include some flexibility so that a medical practitioner may bend a finger or thumb that the protective guard is positioned on. The dorsal portion may include grooves that are positioned in the dorsal portion to allow the dorsal portion to flex during use. The protective guard may be rotated on a finger or thumb during use to change the location of the protective material.

Protective material of a protective guard may be dyed a different color than less protective or retentive material of the protective guard. For example, the protective portion of a protective guard may be red, orange, yellow, green, or blue, while the less protective portion of the protective guard may be uncolored or skin colored. A portion of the protective guard may be made of a transparent or semi-transparent material. Alternately, a protective portion of a protective guard may be painted or otherwise colored a different color than other portions of the protective guard. The color difference between the penetration resistant portion and the less penetration resistant portions of a protective guard may allow a medical practitioner to maintain awareness of the location of a protective portion of the guard during a medical procedure. The protective portion of a protective guard may be any color that contrasts with a user's skin and/or less protective sections of the protective guard.

A protective portion of a protective guard may have a longer length than a less protective or retentive portion of the protective guard. The smaller length of the retentive portion may promote the ability to flex and bend a finger while wearing the protective guard. The smaller length of the retentive portion may also allow a pad of the finger or thumb upon which the protective guard is placed to remain uncovered during use so that the protective guard does not interfere with a user's ability to register tactile sensations through the finger or thumb pad.

A ventral or retentive portion of a protective guard may be made of a flexible material with some penetration resistance. The retentive portion of a protective guard may be formed of an elastomeric polyvinylchloride compound; such as, but not limited to Flexchem®, which is supplied by Tekni-Plex Co. of New Jersey. In an embodiment, an retentive portion is formed of a 0.75 millimeter thick, 65 Shore A durometer hardness, elastomeric polyvinylchloride material. The resistance of the material to puncture by a 27 gauge needle may be over four times greater than penetration resistance of a double pair of latex gloves, each glove having a thickness between about 0.05 millimeters and 0.2 millimeters. The penetration resistance of the material to puncture by a 20 gauge needle may be over eight times greater than the penetration resistance of a double pair of latex gloves, each glove having a thickness between about 0.05 millimeters and 0.2 millimeters.

A dorsal or protective portion of a protective guard may be made of a penetration resistant material that has some flexibility. The flexibility of the protective portion and the shape of the protective guard may allow a medical practitioner to bend a finger or thumb upon which is positioned the protective guard. The protective portion of the protective guard may be formed of an elastomeric polyvinylchloride compound; such as, but not limited to, Unichem®, which is supplied by Tekni-Plex Co. of New Jersey. In an embodiment, a protective portion is formed of a 0.80 millimeter, 90 Shore A durometer hardness, polyvinylchloride material. The resistance of the material to puncture by a 27 gauge needle may be over twenty-six times greater than penetration resistance of a double pair of latex gloves, each glove having a thickness between about 0.05 millimeters and 0.2 millimeters. The penetration resistance of the material to puncture by a 20 gauge needle may be over fifty-one times greater than the penetration resistance of a double pair of latex gloves, each glove having a thickness between about 0.05 millimeters and 0.2 millimeters. In some embodiments, grooves may be formed in the protective portion of the guard to increase the flexibility of the guard.

In some applications, a protective guard may be rotated on a thumb or finger to change a position of a primary protective portion of the protective guard. For example, if the protective guard is positioned over a surgical glove, the guard may be rotated during use to change the position of the protective portion of the protective guard from the back of the finger to the front of the finger. A color difference between a protective portion of the protective guard and a less protective portion of the guard may allow a medical practitioner to visually confirm that the protective portion of the guard is positioned where desired.

A protective guard may include a lip at an end that will be closest to a fingertip when the guard is placed on a finger or thumb. The end may contact a fingernail or a fingertip during use to properly position the protective guard and inhibit the guard from advancing too far up a user's finger or thumb. The lip may be an indicator of an insertion depth of the protective guard on a user's finger or thumb.

A portion of a protective guard may be made of a protective material. The protective material may include, but is not limited to, a poly-paraphenylene terephthalamide or similar material, or a polymerized fluorocarbon, such as polytetrafluoroethylene or similar material. In embodiments, the protective material may be Kevlar® or Teflon®, which are available from E. I. du Pont de Nemours and Company of Delaware. The protective material may be positioned only on a selected portion of the protective guard as a layer, or the protective material may form substantially all of a puncture resistant portion of a protective guard. If the protective material is positioned on only a selected portion of the protective guard, the protective layer may be a different color than a puncture resistant portion of the protective guard, which may be of different color than other portions of the protective guard.

An advantage of a protective guard is that the guard includes a puncture and penetration resistant protective portion and a retentive portion. The protective portion may include some flexibility and the retentive portion may include significant puncture and penetration resistance. The protective portion and the retentive portion may result in a protective guard that provides a large degree of puncture and penetration resistance while still remaining easy to manipulate during a medical procedure. The protective guard may not include portions that cover a significant portion of the pad of a finger or thumb so that a user retains the ability to feel tactile sensations through the finger or thumb. A medical practitioner may retain tactile sense in the protected finger or thumb while wearing the protective guard.

An advantage of a protective guard may be that the guard has a substantial amount of flexibility. The substantial amount of flexibility may allow the protective guard to conform to a user's finger or thumb when the finger or thumb is flexed without being uncomfortable to the user.

An advantage of a protective guard is that the protective guard may be multi-colored. A protective portion of the protective guard may be a different color than less protective portions of the guard. For example, a dorsal side of a protective guard that is puncture and penetration resistant may have a green color, while a ventral side of the protective guard may have a tan color. The multi-colored guard may provide a conscious reminder to a medical practitioner of the protective portion of the guard.

Another advantage of a protective guard may include that the protective guard has a layer or layers of additional protective material. Another advantage of a protective guard is that the guard may have a lip at an end of the guard that limits an insertion depth of the guard on a user's finger or thumb. Further advantages of protective guards may include that the guards are safe, durable, light weight, simple, efficient, reliable, disposable, comfortable, and inexpensive; yet the guards may also be easy to manufacture, don, and use.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

BRIEF DESCRIPTION OF THE DRAWINGS

Further advantages of the present invention will become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 1:
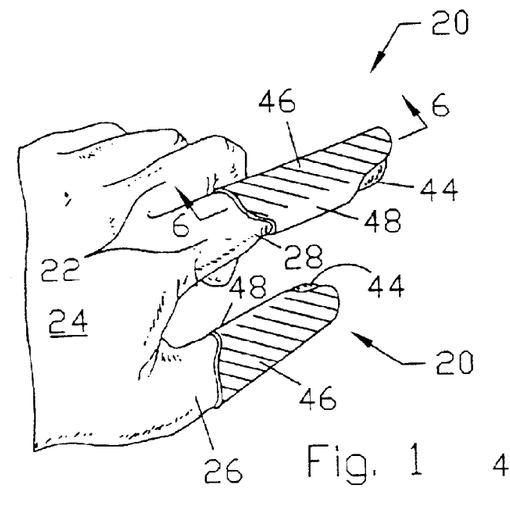
FIG. 1 shows a perspective view of a hand with protective guards positioned on an index finger and a thumb.

Referring to the drawings and particularly to FIG. 1, a protective guard for a finger or thumb is designated by reference numeral 20. A medical practitioner may use a protective guard 20 during a medical procedure to reduce the risk of puncturing or otherwise producing a percutaneous injury during the medical procedure. FIG. 1 shows a protective guard 20 positioned on finger 22 of hand 24; and a protective guard positioned on thumb 26 of the hand. Using protective guards 20 to reduce the risks of forming skin openings during medical procedures may reduce the transmission of disease and pathogens between medical practitioners and patients. Preventing a puncture or skin opening in a medical practitioner may prevent emotional trauma associated with producing an accidental opening during a medical procedure. Medical practitioners may be, but are not limited to, doctors, physician assistants, nurses, dentists, dental assistants, or oral hygienists. A medical procedure may include, but is not limited to, an invasive medical operation, a dental cleaning or procedure, insertion of a needle into a patient to inject or draw fluid, performing laboratory tests on tissue or fluid samples, and cleaning or disposing of used instruments or needles.

Figure 2:
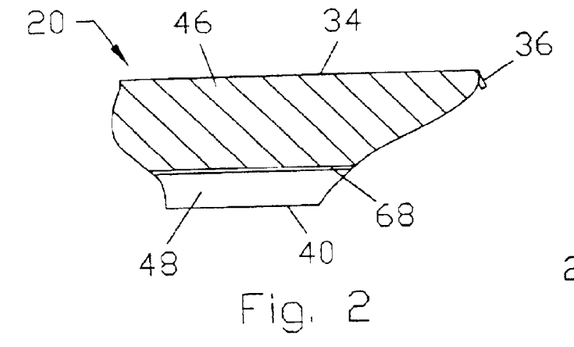
FIG. 2 shows a front view of a protective guard, wherein a protective portion of the guard has a green color.
Figure 3:
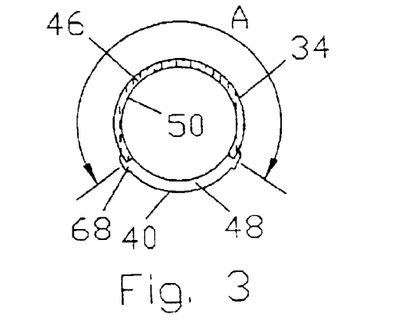
FIG. 3 shows an end view of a protective guard wherein a protective portion of the guard is thicker than a less protective portion of the guard, wherein a protective portion of the guard has a purple color.
Figure 4:
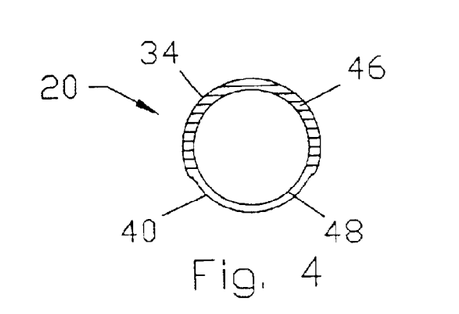
FIG. 4 shows an end view of a protective guard wherein a protective portion of the guard is thinner than a less protective portion of the guard, wherein a protective portion of the guard has a blue color.
Figure 5:
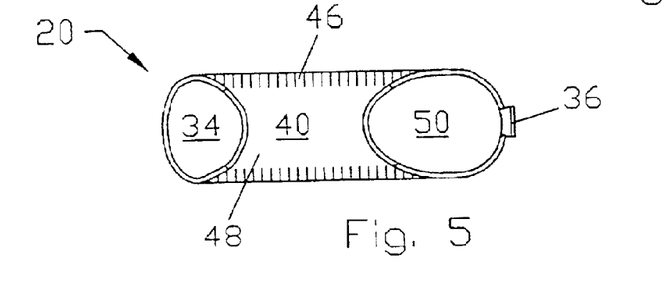
FIG. 5 shows a bottom view of the protective guard, wherein a protective portion of the guard has an outer surface that is red.

A protective guard 20 may be an elongated tubular member that extends generally from the medial joint 28 of a finger 22 or thumb 26 to an end of the finger or thumb. FIG. 2 shows a front view of an embodiment of a protective guard 20. FIGS. 3 and 4 show end views of embodiments of protective guards 20. FIG. 5 shows a bottom view of a protective guard 20. The protective guard 20 may be a semi-rigid structure. The protective guard 20 may have a shape that does not cover creases formed by the bottom portion of the medial joint 28 on ventral or front surface 30 of the finger 22 or thumb 26, as shown in FIG. 6.

Figure 6:
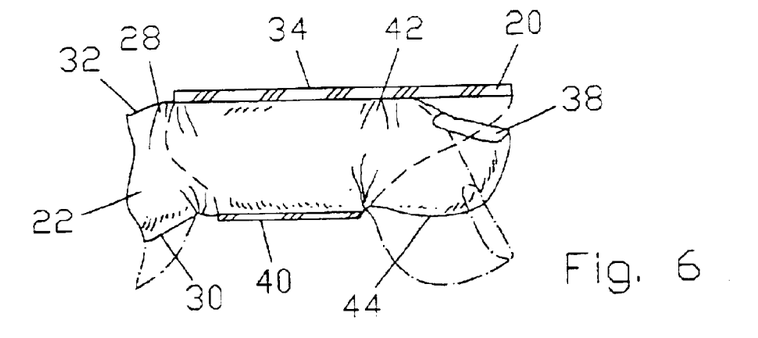
FIG. 6 shows a cross sectional view of a protective guard positioned on a finger (the finger is not shown in cross section) taken substantially along plane 6—6 of FIG. 1.

FIG. 6 shows an embodiment of a protective guard 20 positioned on a finger 22. An upper portion of the protective guard 20 may cover or stop in the creases of the medial joint 28 on dorsal or back surface 32 of the finger 22. The shape of the protective guard 20 may allow the medical practitioner to retain flexibility of the medial finger joint 28 when the guard is placed on the finger 22.

Dorsal portion 34 of a protective guard 20 may extend beyond a fingertip of a finger 22 when the guard is placed on the finger or thumb. The protective guard 20 may optionally include lip 36. FIGS. 2 and 5 show an embodiment of a protective guard 20 that includes a lip 36. Contact of the lip 36 against fingernail 38 (shown in FIG. 6) or end surface of a fingertip may inform a user that the protective guard 20 is fully positioned on a finger 22. The lip 36 may also inhibit the protective guard 20 from sliding up the finger 22 during use. In some embodiments, protective guards 20 do not include lips, such as in the embodiment shown in FIG. 6.

Ventral portion 40 of a protective guard 20 may stop short of creases of distal joint 42 of a finger 22 or thumb 26. A medical practitioner may retain flexibility of the distal finger joint 42 when the protective guard 20 is placed on the finger 22. The protective guard 20 may have a shape at a fingertip end or thumb tip end of the guard that allows pad 44 of the medical practitioner's finger 22 or thumb 26 to remain uncovered when the protective guard 20 is placed on the finger or thumb. Leaving the pad 44 uncovered by the protective guard 20 may allow the medical practitioner to retain the ability to register tactile sensations through the pad 44 during a medical procedure. The ability to flex the finger joints 28, 42 while wearing the protective guard 20 and the ability to feel tactile sensations may allow a medical practitioner to palpate and manipulate tissue during a medical procedure while wearing the protective guard. A ventral portion 40 of the protective guard 20 may be positioned between the medial joint 28 and the distal joint 42 when the protective guard is positioned on the finger 22 or thumb 26.

Figure 7:
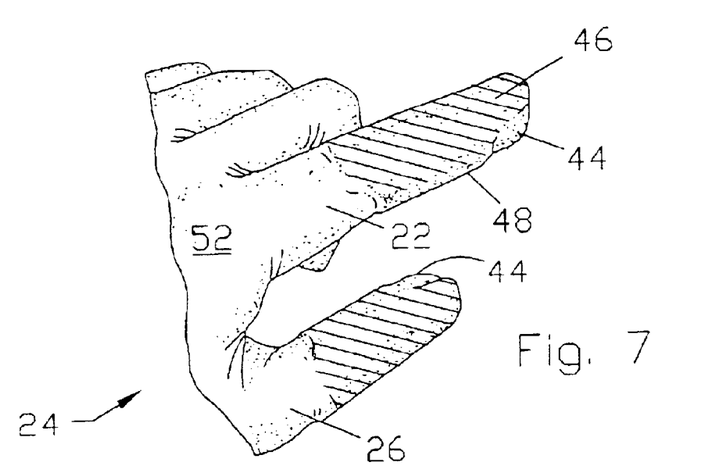
FIG. 7 shows a perspective view of a hand with protective guards positioned on an index finger and a thumb, with a glove positioned over the protective guards, and wherein the color of a protective portion of the guard is visible through the glove.
Figure 8:
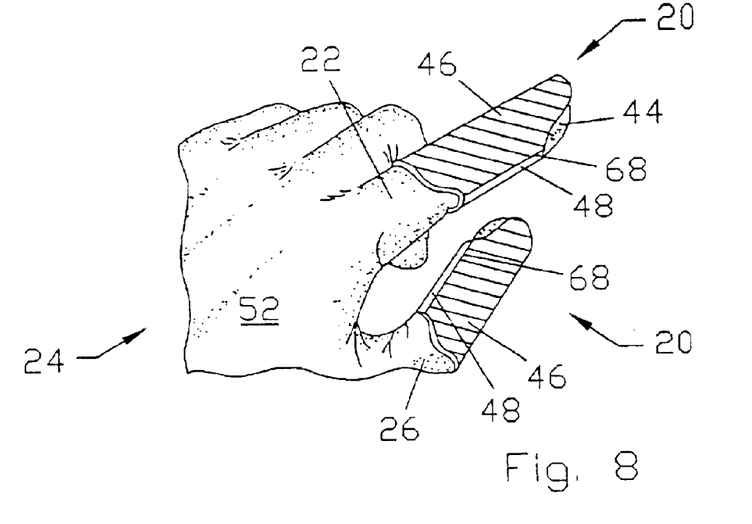
FIG. 8 shows a perspective view of a hand with a glove, and with protective guards positioned over the glove on an index finger and a thumb.

As shown in FIG. 5, a dorsal portion 34 of a protective guard 20 may have a longer length than a ventral portion 40 of the protective guard. The shorter length of the ventral portion 40 may facilitate bending and flexing of a user's finger 22 or thumb 26 when the protective guard 20 is positioned on the finger or thumb. The shorter length of the ventral portion 40 may also allow a portion of a user's finger or thumb pad 44 to remain uncovered when the protective guard 20 is positioned on the user's finger 22 or thumb 26, as shown in FIGS. 1, 7 and 8.

A protective guard 20 may be configured to be placed on a finger 22 of a medical practitioner. Alternately, a protective guard 20 may be configured to be placed on a thumb 26 of a medical practitioner. During a medical procedure, a medical practitioner may place a protective guard 20 on one or more fingers 22 and/or on a thumb 26 of a hand 24. In a typical application, protective guards 20 are placed on a non-dominant hand 24 of the medical practitioner. A protective guard 20 for a thumb 26 may have a shorter length and a wider diameter to account for a size difference between a thumb and a finger 22. Several different sizes of protective guards 20 for fingers 22 and for thumbs 26 may be produced to accommodate various users with different sizes of fingers and thumbs. The protective guards 20 may be removed and disposed of after use.

A protective guard 20 may include protective portion 46 and a less protective portion 48. The protective portion 46 may be resistant to punctures, penetrations and tears. In an embodiment, the protective portion 46 may include dorsal portion 34 of the protective guard 20, and the less protective or retentive portion 48 may include the ventral portion 40 of the protective guard. The less protective portion 48 of the protective guard 20 may be formed of an elastic material. The less protective portion 48 may extend between a medial finger joint 28 and a distal finger joint 42 when the protective guard 20 is placed on a finger 22. The less protective portion 48 may be a retentive portion of a protective guard 20 that keeps the guard on a user's finger 22 or thumb 26. A circumference of inner surface 50 (shown in FIGS. 3–5) of the protective guard 20 may be smaller than an outer circumference of a finger 22 or thumb 26 that the guard is to be placed on. The elastic material may expand when the protective guard is positioned on the finger 22 or thumb 26. The elastic material may exert compressive force on the finger 22 or thumb 26 to hold protective guard 20 on the finger or thumb. The elastic properties of the material may form a seal between the finger 22 or thumb 26 and the protective guard 20. The seal may inhibit fluid from contacting the skin of the finger protected by the guard. Grooves may be formed in the elastic material (not shown) that may allow increased flexibility of protective guard 20.

A protective portion 46 of a protective guard 20 may be a different color than a less protective portion 48 of the guard. FIGS. 1, 7 and 8 show embodiments of protective guards 20 where protective portions 46 of the guards are different in color than less protective portions 48 of the guards. FIG. 1 shows protective guards 20 positioned on an index finger 22 and thumb 26 of hand 24. FIG. 7 shows protective guards 20 positioned on index finger 22 and thumb 26 with surgical glove 52 positioned over the guards. FIG. 8 shows the protective guards 20 positioned over a surgical glove on index finger 22 and thumb 26 of hand 24. In an alternate embodiment (not shown), a hand 24 may be covered by a surgical glove 52 with one protective guard 20 located under the glove, and with a second protective guard positioned over the glove. For example, a protective guard 20 may be positioned on a thumb 26, a glove 52 may be pulled over the hand 24, and a second protective guard may be positioned on an index finger and/or middle finger.

Material that forms the protective portion 46 of a protective guard 20 may be dyed a different color than the material that forms the less protective portion 48. Alternately, the protective portion 46 may be painted a different color than the less protective portion 48. The color of the protective portion 46 may be a vivid color that results in a marked contrast with the color of the less protective portion 48 of the protective guard 20, and with the color of the user's finger 22 or thumb 26. The color of the protective portion 46 may be, but is not limited to, red, orange, yellow, green, or blue. The color of the less protective portion 48 may be the natural color of the material used to form the portion, or any color that provides a noticeable contrast with the color of the protective portion 46 and/or a noticeable contrast with the color of a user's skin. Preferably, the colors of the protective portion 20 and the less protective portion 48 of the protective guard 20 provide a contrast that allows a medical practitioner to distinguish between the two portions when the protective guard is covered by a surgical glove 52 or other covering. The colors of the protective portion 46 and the less protective portion 48 may contrast with the skin color of a user's fingers 22 and/or thumb 26 so that a user may easily visualize the limits of protection afforded by the protective guard 20.

Protective portion 46 and less protective portion 48 of a protective guard 20 may be made of biocompatible materials. The protective guard 20 may be made of inexpensive materials. The protective guards 20 used during a medical procedure may be disposed of after the medical procedure. The protective portion 46 and the less protective portion 48 of the protective guard 20 may include elastomeric materials. The material used to form the protective portion 46 of a protective guard 20 may include, but is not limited to, UniChem® polyvinylchloride. The material used to form the less protective portion 48 of a protective guard 20 may include, but is not limited to, FlexChem® polyvinylchloride. UniChem® and FlexChem® may be obtained from Tekni-Plex Co. of New Jersey. The protective portion 46 and the less protection portion 48 may be made of chemically similar materials so that a strong bond is formed between the two portions at interfaces between the two materials during formation of the protective guard 20. The strong bond may inhibit separation of the two materials. If the protective portion 46 and the less protective portion 48 do not bond well together, a bonding agent may be used to ensure that a strong bond is formed at interfaces between the two portions.

A protective portion 46 may include or be a protective material, such as, but not limited to Kevlar® (a polyparaphenylene terephthalamide or similar material) or Teflon® (a polytetrafluoroethylene or similar material). Kevlar® and Teflon® may be obtained through E.I. du Pont de Nemours and Company of Delaware. If the protective guard 20 includes a layer of a protective material within the protective portion 46, the layer may be a different color, tint, or shade than other sections of the protective portion. The less protective portion 48 may also include a layer or layers of protective material.

In some embodiments of protective guards 20, the protective guards may taper from large ends to a smaller ends. A taper of the protective guard 20 may substantially correspond to a taper of a finger 22. The small end of the protective guard 20 may be positioned near a fingertip, and the large end may be positioned near or over a medial joint 28 of the finger 22 when the protective guard is positioned on a user's finger. Tapering protective guards 20 may be formed by any formation technique, including but not limited to injection molding or reaction injection molding.

Figure 9:
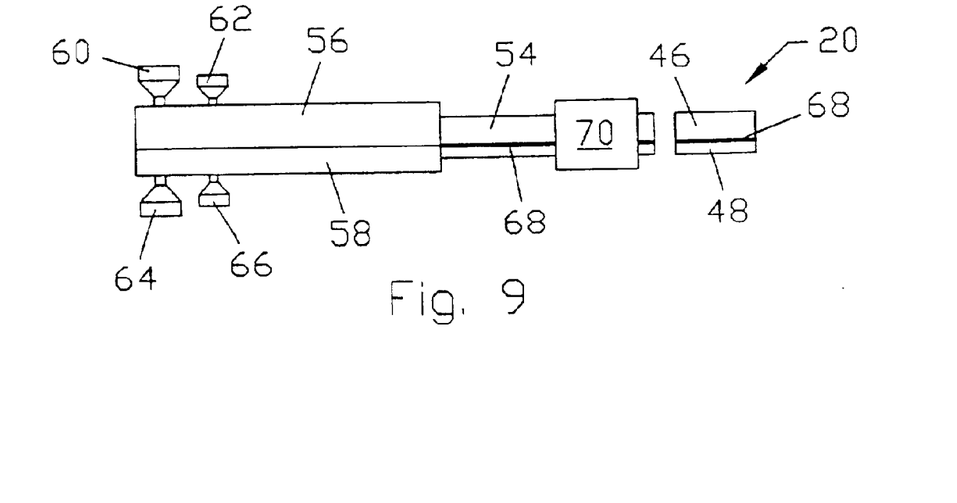
FIG. 9 shows a schematic view of processing equipment that may be used to form a protective guard.

In some embodiments a protective guard 20 may be substantially untapered. A protective guard 20 may be cut from tube 54 formed using a dual extrusion procedure. FIG. 9 shows a schematic diagram of processing equipment that may be used to form a tube 54. The processing equipment may include first extruder 56 that is coupled to second extruder 58. The first and second extruders 56, 58 may form a tube 54. Storage vessel 60 may supply a first material to extruder 56. Dye storage vessel 62 may supply dye that is mixed with the first material. The first material may form a protective portion 46 of a protective guard 20. The color of the protective portion 46 may contrast with a user's skin color and with a color of material used to form a less protective portion 48 of the protective guard 20. Storage vessel 64 may supply a second material to extruder 58 for forming less protective portion 48. Dye storage vessel 66 may supply dye that is mixed with the second material to change the color of the less protective portion 48.

A first extruder 56 may form a first material into an arcuate protective portion 46 with angle A (shown in FIG. 3) from end to end between about $\pi/2$ radians (or about 90°) and about $2\pi$ radians (or about 360°). In embodiments, the angle A is within an angular range from end to end between about $\pi$ radians (or about 180°) and $3\pi/2$ radians (or about 270°), and in an embodiment, the angular range from end to end is about $5\pi/4$ radians (or about 225°). The protective portion 46 may taper or be irregular so that the angular range of the protective portion varies along a length of the protective guard 20. The second material may be formed in an arcuate shape so that the protective portion 46 and the less protective portion 48 form a substantially ring-shaped protective guard 20 when bonded together. As the first material and the second material are bonded together, bead 68 may form at the intersection of the two materials. The bead 68 may be an overlapping layer of the second material. The bead 68 may be formed along an axial length of a tube formed by extruders 56, 58.

After formation of a tube 54 by extruders 56, 58, the tube may be sent to cutting machine 70. A tube 54 formed by extruders 56, 58 may automatically be sent to the cutter 70, or a tube may be manually transferred to the cutter. A bead 68 between a protective portion 46 and a less protective portion 48 of a tube 54 may serve as a guide for cutter 70 to ensure that the tube is properly oriented relative to a cutter or cutters of the cutting machine. The bead 68 may also inhibit tearing or separation of a formed protective guard 20 at an interfaces between the protective portion 46 and the less protective portion 48.

Figure 10:
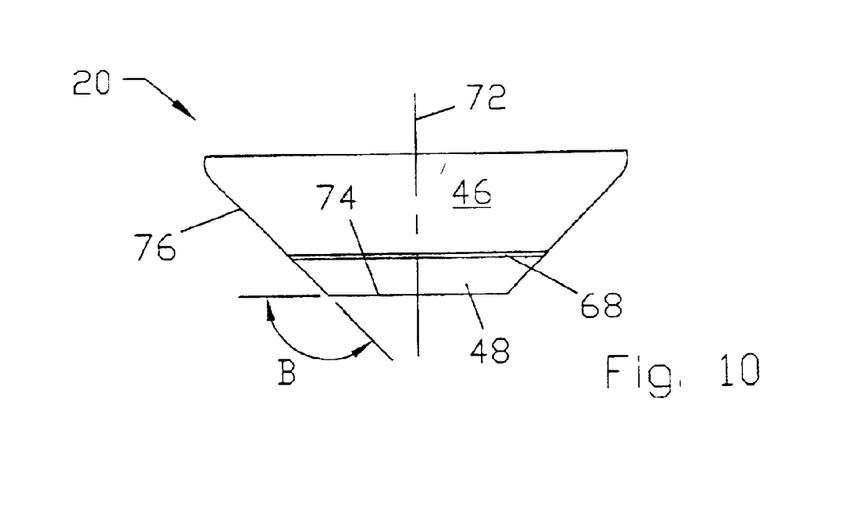
FIG. 10 shows a front view of a symmetric protective guard.

A cutting machine 70 may form an intermediary protective guard that may be further trimmed to a desired shape, or the cutting machine may produce a formed protective guard 20. FIG. 10 shows an embodiment of a protective guard 20 after the guard has passed through cutting machine 70. The cutting machine 70 may produce an embodiment of a protective guard 20 that has a symmetrical shape about axis 72. Other cutting machines 70 may produce protective guards 20 that do not have symmetrical shapes, such as the embodiment of a protective guard 20 shown in FIG. 2. In the protective guard embodiment shown in FIG. 10, angle B between bottom 74 of the protective guard 20 and end 76 of the protective guard may range between 160° to about 90°. In other embodiments, the angle B may be between about 120° and 140°, and may preferably be about 135°.

Materials with different material properties may be chosen to form the protective and less protective portions 46, 48 of a protective guard 20. Table 1 shows some material properties for materials that may be used to form a protective guard 20. The penetration load is the maximum load that the material resists before being penetrated by a needle of the indicated gauge. Two representative needle sizes were chosen to be used in the puncture/penetration tests: a thick needle size (20 gauge) and a thin needle size (27 gauge). Material 1 in Table 1 is two latex gloves, and is included as a reference for puncture resistant properties of other materials.

Materials for a protective guard 20 may be chosen based in part upon resistance to puncture and flexibility. The material for a protective portion 46 of a protective guard 20 may be chosen so that the material has a penetration resistance to a 20 gauge needle greater than about 2.0 N, and a penetration resistance to a 27 gauge needle greater than about 1.3 N. The material for a less protective portion 48 of a protective guard 20 may be chosen so that the material has a penetration resistance to a 20 gauge needle that is greater than about 1.0 N, and a penetration resistance to a 27 gauge needle greater than about 0.4 N. Less or greater puncture resistance limits may be chosen for the protective and less protective portions 46, 48 of a protective guard 20.

TABLE 1

| Material | 1 | 2 | 3 | 4 | 5 | 6 |
|---|---|---|---|---|---|---|
| Shore A durometer hardness | (two latex gloves) | 65 | 85 | 85 | 90 | 90 |
| Thickness (mm) | 0.20 | 0.75 | 0.50 | 0.80 | 0.53 | 0.80 |
| Bending Load at 45° (N) | NA | 0.033 | 0.035 | 0.148 | 0.094 | 0.299 |
| Penetration Load for 20 gauge needle (N) | 0.17 | 1.51 | 2.44 | 6.84 | 3.6 | 8.8 |
| Penetration Load for 27 Gauge Needle (N) | 0.14 | 0.59 | 1.56 | 2.64 | 2.06 | 3.75 |
| Ratio of Penetration Load to Bending Load for 20 Gauge Needle | NA | 46 | 70 | 46 | 38 | 29 |
| Ratio of Penetration Load to Bending Load for 27 Gauge Needle | NA | 17 | 45 | 18 | 22 | 13 |

Thicknesses of materials for a protective guard 20 may be chosen so that the protective guard has desired penetration and flexibility properties. A thickness of a protective portion 46 of a protective guard 20 may be less, equal or greater than a thickness of a less protective portion 48. For example, FIG. 3 shows an end view of an embodiment of a protective guard 20 that has a thicker protective portion 46 and a thinner less protective portion 48. The protective portion 46 may be formed of 90 Shore A durometer/0.80 mm polyvinylchloride elastomer, and the less protective portion 48 may be formed of 85 Shore A durometer/0.50 mm polyvinylchloride elastomer. FIG. 4 shows an end view of an embodiment of a protective guard 20 that has a thinner protective portion 46 and a thicker less protective portion 48. The protective portion 46 may be formed of 85 Shore A durometer/0.50 mm polyvinylchloride elastomer; and the less protective portion 48 may be formed of 65 Shore A durometer/0.75 mm polyvinylchoride elastomer.

The values in the last two rows of the table indicate the ratio of maximum bending load to penetration for 20 and 27 gauge needles, respectively. These ratios may identify the degree to which flexibility is compromised for increased penetration resistance in a protective guard 20. For example, a large ratio (such as 70 and 45 for 85 Shore A durometer/0.50 mm thick material) identifies a material that may provide increased protection with minimal compromise in flexibility. A small ratio (such as 29 and 13 for 90 Shore A durometer/0.80 mm thick material) identifies a material that may provide increased protection but may also be stiff or relatively inflexible. Having materials that are protective and also flexible allows a protective guard 20 to be formed that provides increased penetration resistance and conforms to a user's finger 22 or thumb 26 during use, even when the user bends or flexes the finger or thumb.

In an embodiment, a protective portion 46 of a protective guard 20 may be made of 85 Shore A durometer/0.50 mm thick material, and a less protective portion 48 of the guard may be made of 65 durometer/0.75 mm thick material. The color of the protective portion 46 may be green. The less protective portion 48 may be a transparent or semi-transparent color that is distinctly different than the color of the protective portion 46. Because the thickness of the protective portion 46 is less than the thickness of the less protective portion 48, the difference in color between the two portions may indicate to a user of the protective guard 20 that the protective portion is actually the thin portion of the protective guard. The protective portion 46 may provide over 14 times the protection of doubled latex gloves 52 to puncture from 20-gauge needles, and over 11 times the protection of doubled latex gloves to puncture from 27-gauge needles. The less protective portion 48 may provide over 8 times the protection of doubled latex gloves 52 to puncture from 20-gauge needles, and over 4 times the protection of doubled latex gloves to puncture from 27-gauge needles.

The values shown in the table are illustrative of several materials that may be used to form protective guards 20 that inhibit or prevent skin penetration during medical procedures by percutaneous injury causing devices. Other materials may be chosen based upon a number of factors, including but not limited to, comfort, elasticity, allergenic properties of the material, and penetration/puncture resistance of the material.

Figure 11:
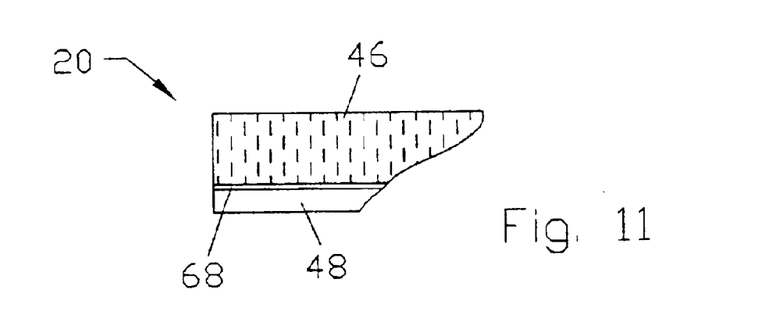
FIG. 11 shows a flexible protective guard with a non-undercut end portion, wherein a protective portion of the guard is purple.

In an embodiment, the materials used to form a protective guard 20 may have a flexibility that allows an end of the protective guard that is placed adjacent to a medial joint 28 to have a substantially cylindrical shape without undercut portions. In other words, the angle B (shown in FIG. 10) for an end of the protective guard 20 may be about 90°. The substantially cylindrical shape may obviate the need to shape the end of the protective guard 20 to provide a user the ability to bend a finger at the medial joint 28. FIG. 11 shows an embodiment of a protective guard 20 where the protective guard is made of materials that allow the protective guard to remain substantially flexible so that an end of the guard does not need to include an undercut portion that allows a user to flex a protected finger. In an embodiment, a material or materials used to form a protective portion 46 of a protective guard 20 may be sufficiently flexible, and may provide sufficient penetration resistance, so that the entire protective guard may be formed only of the material or materials of the protective portion. Grooves (not shown) may be formed in the protective portion to increase the flexibility of the protective portion. This may allow some flexing of the flexible portion when the finger or thumb of the user is bent.

A protective guard 20 may be placed on a finger 22 or thumb 26 immediately adjacent to skin. Alternately, the protective guard 20 may be placed over a surgical glove 52 or other covering surrounding a user's skin. A user may pull the protective guard 20 on the finger 22 or thumb 26. The protective guard 20 may provide protection against penetration or opening of the medical practitioner's skin during a medical procedure; yet the protective guard may still allow the user the ability to flex and bend a protected digit. A digit refers to a finger 22 or thumb 26. During the medical procedure, the protective guard 20 may be rotated on the digit to protect a desired portion of the digit. A difference in color between a protective portion 46 and less protective portion 48 may allow a user to know where the protective portion of the protective guard 20 is located during the medical procedure.

A protective guard 20 may be placed on a finger 22 or fingers of a hand 24 of a user. A protective guard 20 may also be placed on a thumb 26 of the user. Typically, the protective guards are placed on selected digits of a non-dominant hand of the user, though protective guards may also be used with a user's dominant hand. The protective guards 20 may protect the user against inadvertent skin penetrations from sharps during a medical procedure while still allowing the user to retain tactile sensations from the finger 22 or thumb 26. Sharps may include, but are not limited to, hypodermic needles; medical, dental and laboratory instruments; and burs and sharp edges or projections of hard tissue and prostheses. As an example of use, protective guards 20 positioned on a user's non-dominant hand 24 may inhibit inadvertent skin penetration from needles held and positioned with the user's dominant hand during a procedure. As another example of use, protective guards 20 positioned on a user's non-dominant hand 24 may inhibit inadvertent skin penetration from a dental scaler if the user's protected finger inadvertently slips from contact with a patient's tooth or gum while the user is removing buildup material from a tooth with the dental scaler.

A protective guard 20 may be formed using an extrusion process. In an embodiment, a polyvinylchloride material that forms a protective portion 46 of a protective guard 20 and a polyvinylchloride material that forms a less protective portion 48 are simultaneously extruded to form the protective guard. The similar properties of the materials may allow the two portions 46, 48 of the protective guard 20 to bond together during the extrusion process. In alternate embodiments, the protective portion 46 is formed separately from the less protective portion 48 and the two portions are subsequently bonded together. The two portions 46, 48 may be bonded together by, but are not limited to being bonded by, heat welding, sonic welding, solvent welding or gluing. After the protective portion 46 and the less protective portion 48 are bonded together, the resulting material may be cut and shaped to form individual protective guards 20. An indentation may be formed at an end of a protective guard 20 to allow a portion of a pad 44 of a user's finger 22 or thumb 26 to remain uncovered by the protective guard when the guard is placed on the finger or thumb. An indentation may be formed at an opposite end of the protective guard 20 to allow the user the ability to bend the medial finger joint 28. Other processes may also be used to produce protective guards 20, including, but not limited to, injection molding and reaction injection molding.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A guard for a digit of a hand, comprising:
    a body;
    a protective portion of the body configured to be penetration resistant; and
    a less protective portion of the body adjacent to the protective portion;
    wherein the protective portion is of a different color than the less protective portion, and
    wherein the color of the protective portion is visible to a user of the guard before use of the guard.

2. The guard of claim 1, wherein a color of the protective portion is visually distinct from a color of the less protective portion.

3. The guard of claim 1, wherein an end of the body is shaped so that a portion of a pad of the digit remains uncovered by the body during use in order for the digit to retain the ability to register tactile sensations.

4. The guard of claim 1, wherein the protective portion comprises poly-paraphenylene terephthalamide.

5. The guard of claim 1, wherein the productive portion comprises polytetra-fluoroethylene.

6. The guard of claim 1, wherein the protective portion comprises an elastomeric material.

7. The guard of claim 1, wherein the less protective portion is adapted to provide at least four times the penetration resistance to a 27-gauge needle during use than a double layer of latex gloves, each glove having a thickness between about 0.05 millimeters and 0.2 millimeters.

8. The guard of claim 1, wherein a portion of the body is shaped to avoid covering a portion of a medial joint to allow the digit the ability to flex during use.

9. The guard of claim 1, wherein the body covers a substantial portion of a medial joint of the digit, and wherein the protective section and the less protective section are flexible to allow the digit to flex during use.

10. The guard of claim 1, further comprising a lip at an end of the body, the lip configured to provide an indicator of an insertion depth of the body on the digit.

11. The guard of claim 1, wherein the color of the protective portion is visible through a covering worn over the body.

12. The guard of claim 1, wherein the protective portion is substantially transparent.

13. The guard of claim 1, wherein the less protective portion is substantially transparent.

14. The guard of claim 1, wherein the body comprises a dorsal portion.

15. The guard of claim 14, wherein the dorsal portion includes the protective portion.

16. The guard of claim 14, wherein the dorsal portion is configured to contact a dorsal portion of the digit during use.

17. The guard of claim 1, further comprising a bead of material formed between the protective portion and the less protective portion.

18. The guard of claim 1, wherein the protective portion has a longer length than a length of the less protective portion.

19. The guard of claim 1, wherein the protective portion has an angular range between about $\pi/2$ radians and about $7\pi/4$ radians.

20. The guard of claim 1, wherein the protective portion has an angular range of about $5\pi/4$ radians.

21. A guard for a digit of a hand, comprising:
    a body having an opening in an end configured to allow a portion of a pad of the digit to remain uncovered by the guard during use, wherein the end comprises a lip configured to provide an indicator of an insertion depth of the body on the digit;
    wherein the body comprises a protective portion having a puncture resistance to a 20-gauge needle of at least about 2 newtons; and wherein a color of the protective portion contrasts with a color of skin of the digit.

22. The guard of claim 21, further comprising a less protective portion, the less protective portion configured to hold the guard on the digit.

23. The guard of claim 22, further comprising a bead of material between the protective portion and the less protective portion.

24. The method of claim 22, further comprising rotating the protective guard during use to change a position of the protective portion of the protective guard to a different portion of the digit.

25. The guard of claim 21, further comprising a less protective portion, the less protective portion having a color visually distinct from the color of the protective portion.

26. The guard of claim 21, wherein the color of the protective portion is visible through a covering worn over the body.

27. The method of claim 21, wherein the protective guard includes a less protective portion, the less protective portion comprising a color that is visibly distinct from the color of the protective portion.

28. A method of producing a protective guard for a digit of a hand, comprising:

forming a protective portion that covers a portion of the digit; and coloring the protective portion so that the protective portion contrasts with a color of the digit so that limits of protection afforded by the protective guard are visualized by a user before use of the protective guard.

29. The method of claim 28, further comprising:

forming a less protective portion; and bonding the protective portion and the less protective portion together to form a body positionable on the digit.

30. The method of claim 29, further comprising forming an indentation in an end of the body that allows a portion of a pad of the digit to remain uncovered during use.

31. The method of claim 29, further comprising forming an indentation in an end of the body that permits bending of a medial joint of the digit.

32. The method of claim 28, further comprising forming a lip at an end of the protective section, the lip configured to provide an indication of insertion depth of the protective portion on the digit.

33. A method of protecting a digit from penetration during a surgical procedure, comprising:

covering a portion of the digit with a protective guard; and using color of a protective portion of the protective guard to guide positioning of the protective portion over part of a back portion of the digit, wherein the protective portion comprises a color that is visibly distinct from a color of the digit.

34. A guard for a digit of a hand, comprising:

a body;

a protective portion of the body configured to be penetration resistant;

a less protective portion of the body adjacent to the protective portion;

a bead of material formed between the protective portion and the less protective portion; and wherein a color difference between the protective portion and the less protective portion allows a user to visually confirm positioning of the protective portion of the guard relative to the digit.

* * * * *